United States Patent [19]

Casale et al.

[11] Patent Number: 4,485,050

[45] Date of Patent: Nov. 27, 1984

[54] PROCESS FOR THE CONTINUOUS PRODUCTION OF TETRACHLOROPHTHALONITRILE IN A FLUIDIZED BED REACTOR

[75] Inventors: Liborio Casale; Giordano Donelli, both of Brescia, Italy

[73] Assignee: Caffaro S.p.A., Milan, Italy

[21] Appl. No.: 494,285

[22] Filed: May 13, 1983

[51] Int. Cl.³ .......................................... C07C 121/56
[52] U.S. Cl. ............................................... 260/465 G
[58] Field of Search ................................... 260/465 G

[56] References Cited

U.S. PATENT DOCUMENTS 3,108,130  10/1963  Haga et al. .................... 260/465 G
3,839,401  10/1974  Lavergne et al. ............. 260/465 G Primary Examiner—Dolph H. Torrence
Attorney, Agent, or Firm—Young & Thompson

[57] ABSTRACT

In an improved process of the continuous production of tetrachlorophthalonitrile, molten atomized phthalonitrile, chlorine, hydrochloric acid and possibly nitrogen are fed simultaneously below the grid of a reactor with a fluidized bed of activated carbon, and the tetrachlorophthalonitrile is separated and recovered continuously by simple cooling.

9 Claims, 1 Drawing Figure

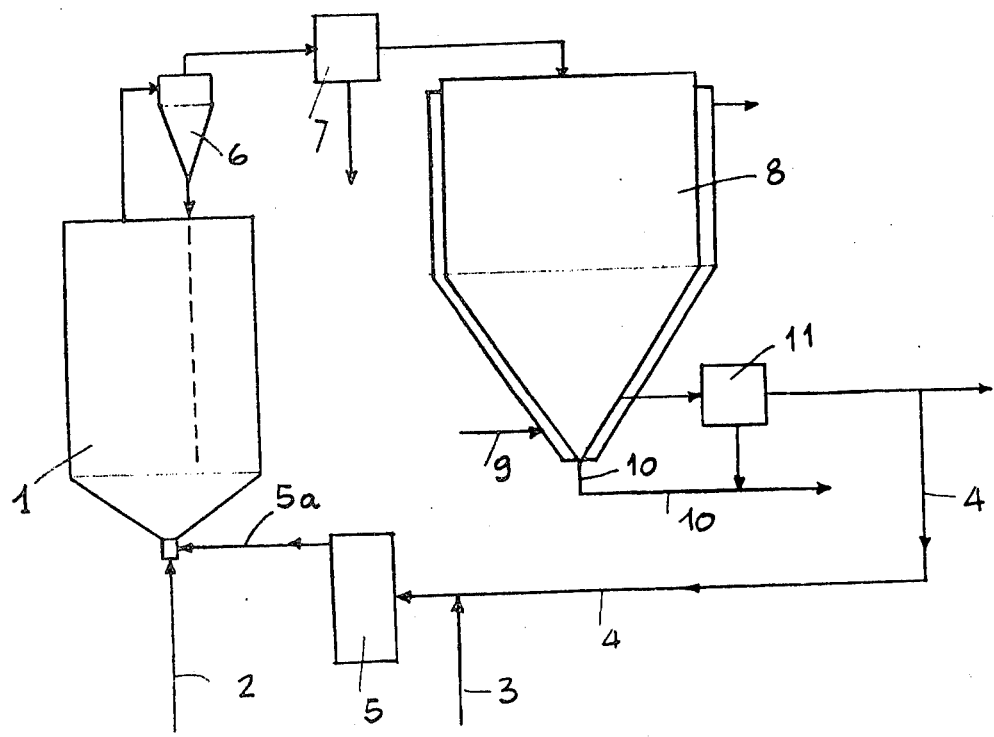

PROCESS FOR THE CONTINUOUS PRODUCTION OF TETRACHLOROPHTHALONITRILE IN A FLUIDIZED BED REACTOR

BACKGROUND OF THE INVENTION

Tetrachlorphthalonitriles, and in particular tetrachloroisophthalonitrile, are widely used for their important phytoprophylatic properties. Studies relative to improvements in the methods and processes which lead to the production of these important compounds are followed threfore with particular attention throughout the world.

The object of the present invention is to provide an improved process for the production of tetrachlorophthalonitriles from the corresponding phthalonitriles by vapour-phase chlorination in a fluidised bed, in a more simple manner and with less sophisticated and less costly apparatus than at the present time.

In this respect, the known fludised bed chlorination processes are generally carried out respecting the following conditions:

in the case of thermolabile organic substances, excessive heating temperatures for relatively long times are avoided so as to prevent the formation of decomposition compounds and polymerisation or limit these latter to very low levels;

the mixture comprising the chlorine and the substance to be chlorinated is prevented from reacting before entering the catalytic layer, so as to prevent uncontrollable premature reactions.

For these reasons, in known processes specified for chlorinating phthalonitriles (such as that described in U.S. Pat. No. 3,839,401) these compounds are fed not in the vapour phase but as molten liquids, and they are injected in an atomised state directly into the body of the catalytic layer, where the reaction chlorine is already present.

Moreover, in many of the known processes for chlorinating phthalonitriles (again such as in that of U.S. Pat. No. 3,839,401), the chlorinated product is recovered from the reaction gas mixture by using water or a solvent which is inert towards chlorine, in order to desublime and extract the reaction product.

It is apparent that each of these processes can be effected only by using apparatus which is sophisticated (required for example to atomise a molten liquid and distribute it in a fluidised bed) and costly (required for example to desublime and extract the product using water or chlorine-resistant organic solvents). Furthermore, transferring these processes to an industrial level poses considerable corrosion problems, problems of a toxicological, ecological and economical character, and plant operation problems.

The interest in simplifying the aforesaid known processes and in particular in simplifying the plant necessary to uprate them to an industrial scale and to enable them to operate is therefore apparent.

The studies of the applicant in this direction have resulted in an improved process which, in addition to attaining these objects, ensures tetrachlorophthalonitrile production at a purity exceeding 98%, this constituting a further important progressive step in comparison with the known art.

SUMMARY OF THE INVENTION

The improved process of the present invention is based on the following considerations:

evaporation of the phthalonitriles can be effected by injecting them in a molten atomised state into a gaseous mixture stream constituted by chlorine, hydrochloric acid and possibly nitrogen, at a temperature which is relatively low compared with the boiling point of phthalonitrile.

The aforesaid procedure is possible because surprisingly under the operating conditions of the present invention the chlorine and phthalonitrile are mutually inert until they reach the catalytic layer.

Consequently, the mixture can be easily prepared in the required proportions and at the required temperature immediately prior to entering the fluidised bed, instead of inside the fluidised bed.

If proceeding as heretofore indicated, the experimentally tested reaction conditions lead to the formation of tetrachlorophthalonitrile at a purity level such that its solidification temperature range is very narrow. Consequently, by cooling the reactor outlet gases, the product desublimes into a crystalline powder which does not adhere to the apparatus walls and which can therefore be easily and continuously recovered without using the highly toxic $CCl_4$, as was generally previously necessary (see again U.S. Pat. No. 3,839,401 for all these aspects). This would not be possible if a higher level of impurities was present, which would cause the formation of eutectic mixture incrustations.

Essentially, the process according to the present invention is therefore characterised in that molten atomised phthalonitrile and a gaseous mixture of chlorine, hydrochloric acid and possibly nitrogen are simultaneously fed by way of the bottom of the reactor to below the grid for the fluidised bed, constituted by activated carbon, the gaseous mixture being in a quantity sufficient to vaporise the phthalonitrile and to keep the activated carbon bed fluidised, and in that following the reaction between $Cl_2$ and phthalonitrile in the fluidised bed with the production of tetrachlorophthalonitrile, this latter is continuously separated by simple cooling. In addition, in the process according to the invention, part of the gaseous mixture leaving the reaction is recycled, and HCl is bled off in a quantity equivalent to that produced by the reaction, once the normal working state has been reached.

DESCRIPTION OF THE PREFERRED EMBODIMENTS

Passing to a more detailed description, the aforesaid process can be said to be effected as follows:

chlorine, hydrochloric acid (and possibly a further inert gas, such as nitrogen) and molten phthalonitrile are fed into a fluidised bed reactor, and particularly into the zone below the bed support grid.

The gas and liquid temperatures and the gas volume are such as to ensure that all the phthalonitrile evaporates at the required temperature, which is much lower than the phthalonitrile boiling point.

The fluidised bed is constituted by activated carbon of suitable particle size to enable it to be fluidised by the gas stream.

The mixture of gases, heated to the required temperature, reacts on passing through the catalytic layer, the heat of reaction being removed from the fluidised bed by known systems.

The gases leaving the fluidised bed are however sufficiently hot to maintain all the reaction products in the vapour state.

The hot gases pass through a cyclone and filter system to be purified of the carbon dust which originates from the fluidised bed.

The gases are then rapidly cooled in a suitable apparatus (desublimator).

The chlorophthalonitrile is discharged continuously from the desublimator and stored, for example using pneumatic conveying.

The cold outlet gases from the desublimator pass through filters which retain the final traces of product in the form of finer powder, this being collected either continuously or periodically.

The gases, purified of the chlorinated organic products, are constituted by hydrochloric acid from the reaction, the excess chlorine and possibly nitrogen which has passed through the apparatus.

Part of these gases are recycled as such to the feed side of the fluidised bed reactor, the necessary make-up chlorine being added.

The remainder, representing the bleed of the hydrochloric acid produced by the reaction and containing the corresponding excess of chlorine, is used to produce hydrochloric acid in solution and dry chlorine by conventional processes. This chlorine can also obviuosly be recycled to the chlorination reactor.

The process is shown diagrammatically on the accompanying drawing which shows that the fluidised bed reactor 1 is fed at its bottom with molten isophthalonitrile directly from 2, and with chlorine and recycle gas from 5a by way of a heater 5, the chlorine originating from 3 and the recycle gas from 4. The reaction products leaving the top of the reactor 1 are fed to a cyclone separator 6 and filter 7 connected in series to separate the entrained carbon dust, and then to a desublimator 8 cooled at 9. The product obtained is recovered from the base of the desublimator 10, and the off-gases are extracted higher up to be filtered in 11, part of them then being removed from 12, and part of them being recycled through 4 as already seen.

The operating conditions to be observed in order to obtain correct operation of the process are as follows:

The phthalonitrile must be maintained at a temperature slightly greater than its melting point, and in the case of isophthalonitrile preferably between 165° and 180° C.

As stated, the gases must be of such a volume and temperature as to evaporate the phthlonitrile without overheating it. Their volumetric composition must be as follows: $Cl_2$ between 30% and 50%; HCl between 30% and 70%; $N_2$ between 0% and 20%.

A mixture of gases (chlorine, hydrochloric acid and possibly a further inert gas) and of phthalonitrile vapour at 180° C. can be obtained by using for example between 1.5 and 5 $Nm^3$ or more of said gases heated to between 250° C. and 350° C. to evaporate 1 kg of molten phthalonitrile at 170° C.

The quantity of chlorine in the gases must be such as to determine a molar ratio of between 7 and 20, and preferably between 10 and 15.

The reaction temperature in the fluidised bed must be between 300° and 450° C., according to the reactor geometry, the reactant residence time in the reaction zone, and other conditions, as known to the expert of the fluidised bed art.

The residence time can vary from 5 to 15 seconds.

The following examples are given to further illustrate the process according to the invention, but without limiting its scope. In particular, the reference therein to the phthalonitrile "iso" isomer has no limiting effect.

EXAMPLE 1

0.5 Kmoles/hour of molten isophthalonitrile with a purity exceeding 99% are fed at 170° C. into an activated carbon fluidised bed reactor below the grid, and are vaporised by 11 Kmoles/hour of a mixture of chlorine, hydrochloric acid and nitrogen at a temperature of 250° C., the chlorine: isophthalonitrile molar ratio being 15.

The evaporation of the molten stream causes the temperature of the gaseous mixture to fall instantly to 170° C., and all the isophthalonitrile passes into the vapour state.

The gaseous mixture passes through the catalytic layer and fluidises it. The heat of reaction is partly removed from the fluidised bed so as to limit the bed temperature and the temperature of the gases leaving the bed to about 350° C. The removed heat is used for heating the inlet gases.

After filtering off the carbon dust, the outlet gases are fed to a cold chamber.

The gases are cooled herein to 40° C., and the chlorination products are collected, the outlet gases passing to a bag filter.

The collected powder is added to that continuously extracted from the condenser. Most of the gas (8.3 Kmoles/hour) is recycled as such, while the remaining 2.7 Kmoles/hour are treated in order to recover the hydrochloric acid from the reaction and to recover the chlorine.

The product obtained, 0.49 Kmoles/hour, has a tetrachloroisophthalonitrile content of 98.5%.

EXAMPLE 2

0.5 Kmoles/hour of isophthalonitrile with a purity exceeding 99% are fed at 170° C. in a molten and atomised state into an activated carbon fludised bed reactor below the grid, and are vaporised by 8 Kmoles/hour of a gaseous mixture of chlorine, hydrochloric acid and nitrogen heated to 300° C., the chlorine: phthalonitrile molar ratio being 10.

The vaporisation of the molten isophthalonitrile causes the temperature of the gaseous mixture to fall instantly to 180° C.

The gaseous mixture passes through the catalytic bed and fluidises it. The heat of reaction is partly removed from the bed so as to limit the temperature of the fluidised bed and of the gases leaving said bed to about 350° C.

The heat removed is used to heat the inlet gases. After filtering off the carbon dust, the outlet gases are fed to a cold chamber where the chlorination products desublime at a temperature of 40° C.

The outlet gases from the desublimator pass through a filter, and the retained powder is combined with the product which is continuously extracted from the desublimator. After filtration, most of the gases (6.4 Kmoles/hour) is recycled, while the remainder (1.6 Kmoles/hour) is treated to recover the hydrochloric acid resulting from the reaction and the excess chlorine.

The product obtained, 0.49 Kmoles/hour, has a tetrachloroisophthalonitrile content of 98.8%.

COMPARISON EXAMPLE 1

Example 1 is repeated but using a silica of 100 m²/g surface area and 300 A average pore diameter as the catalytic bed instead of activated carbon.

Only 3% of the initial isophthalonitrile is converted into tetrachloroisophthalonitrile.

COMPARISON EXAMPLE 2

Example 1 is repeated but using wood charcoal as the catalytic bed instead of activated carbon.

Only 2% of the initial isophthalonitrile is converted to tetrachloroisophthalonitrile.

We claim:

1. A process for the continuous production of tetrachlorophthalonitrile in a fluidised bed reactor, characterised in that molten atomised phthalonitrile and a gaseous mixture of chlorine, hydrochloric acid and possibly nitrogen are simultaneously fed by way of the bottom of the reactor to below the grid for the fluidised bed, constituted by activated carbon, the gaseous mixture being in a quantity sufficient to vaporise the phthalonitrile and to keep the activated carbon bed fluidised, and in that following the reaction between $Cl_2$ and phthalonitrile in the fluidised bed with the production of tetrachlorophthalonitrile, this latter is continuously separated by suitable cooling.

2. A process as claimed in claim 1, wherein part of the gaseous mixture leaving the reaction is recycled, and HCl is bled off in a quantity equivalent to that produced by the reaction, once the normal working state has been reached.

3. A process as claimed in claim 1, wherein the initial phthalonitrile is isophthalonitrile, and the final product is tetrachloroisophthalonitrile.

4. A process as claimed in claim 1, wherein the molten isophthalonitrile is fed at a temperature of between 165° and 180° C. to the bottom of the fluidised bed, below the grid.

5. A process as claimed in claim 1, wherein the initial chlorine: isophthalonitrile molar ratio is between 7 and 20.

6. A process as claimed in claim 1, wherein the gaseous mixture which is fed by way of the bottom of the apparatus to evaporate the phthalonitrile and fluidise the bed has the following composition: $Cl_2$ from 30% to 50% by volume, HCl from 30% to 70% by volume $N_2$ from 0% to 20% by volume.

7. A process as claimed in claim 1, wherein the reaction is carried out at a temperature of between 300° and 450° C. for a residence time of between 5 and 15 seconds.

8. A process as claimed in claim 1, wherein the tetrachloroisophthalonitrile separated from the gaseous reaction mixture by desublimation by simple cooling is recovered continuously without the uses of solvents, in the form of a crystalline powder.

9. A process as claimed in claim 1, wherein most of the gaseous mixture originating from the separation of the tetrachloroisophthalonitrile is recycled and made-up with fresh chlorine to form the feed to the fluidised bed, the remainder being bled off.

* * * * *

UNITED STATES PATENT AND TRADEMARK OFFICE
CERTIFICATE OF CORRECTION

PATENT NO. : 4,485,050

DATED : November 27, 1984

INVENTOR(S) : Liborio CASALE et al.

It is certified that error appears in the above—identified patent and that said Letters Patent is hereby corrected as shown below:

In the heading, recite the claim to priority of Italian application No. 21231 A/82, filed May 13, 1984.

Signed and Sealed this

Sixteenth Day of July 1985

[SEAL]

Attest:

DONALD J. QUIGG

Attesting Officer  Acting Commissioner of Patents and Trademarks